US007188031B1

(12) United States Patent
Okamoto et al.

(10) Patent No.: US 7,188,031 B1
(45) Date of Patent: Mar. 6, 2007

(54) METHOD FOR ACQUIRING INFORMATION OF A BIOCHIP USING TIME OF FLIGHT SECONDARY ION MASS SPECTROMETRY AND AN APPARATUS FOR ACQUIRING INFORMATION FOR THE APPLICATION THEREOF

(75) Inventors: Tadashi Okamoto, Kanagawa (JP); Hiromitsu Takase, Tochigi (JP); Hiroyuki Hashimoto, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 99 days.

(21) Appl. No.: 10/601,777

(22) Filed: Jun. 24, 2003

(30) Foreign Application Priority Data

Jun. 28, 2002 (JP) ............................. 2002-191208
Jun. 6, 2003 (JP) ............................. 2003-161862

(51) Int. Cl.
*G01N 33/48* (2006.01)
*G01R 23/02* (2006.01)
*C12Q 1/00* (2006.01)
*C12M 1/34* (2006.01)

(52) U.S. Cl. .................... 702/19; 435/4; 435/287.9; 250/424; 250/309

(58) Field of Classification Search ................ 250/309, 250/423; 702/19, 20
See application file for complete search history.

(56) References Cited

U.S. PATENT DOCUMENTS

| | | | | |
|---|---|---|---|---|
| 4,983,831 | A | 1/1991 | Migeon et al. ............. | 250/309 |
| 5,008,537 | A | 4/1991 | Toita et al. .................. | 250/309 |
| 5,405,783 | A | 4/1995 | Pirrung et al. ............. | 436/518 |
| 5,491,062 | A | 2/1996 | McKenzie et al. ............. | 435/6 |
| 5,563,410 | A | 10/1996 | Mullock ..................... | 250/288 |
| 5,589,685 | A | 12/1996 | Jen Wu et al. ............ | 250/282 |
| 5,601,980 | A | 2/1997 | Gordon et al. ................ | 435/6 |
| 5,633,495 | A | 5/1997 | Niehuis et al. ............ | 250/287 |
| 5,821,060 | A | 10/1998 | Arlinghaus et al. ........... | 435/6 |
| 6,002,128 | A | 12/1999 | Hill et al. .................... | 250/287 |
| 6,027,890 | A | 2/2000 | Ness et al. ..................... | 435/6 |
| 6,137,110 | A * | 10/2000 | Pellin et al. ............. | 250/423 P |
| 6,384,237 | B1 | 5/2002 | Suzuki et al. ................. | 549/13 |
| 6,476,215 | B1 | 11/2002 | Okamoto et al. ......... | 536/25.3 |
| 2001/0055813 | A1 | 12/2001 | Winograd et al. ........... | 436/89 |
| 2002/0074517 | A1 | 6/2002 | Krutchinsky et al. .... | 250/492.1 |
| 2004/0259088 | A1 | 12/2004 | Okamoto et al. ............. | 435/6 |

FOREIGN PATENT DOCUMENTS

| | | |
|---|---|---|
| DE | 31 44 604 A1 | 5/1983 |
| EP | 0 378 077 A2 | 7/1990 |
| JP | 60-49252 | 3/1985 |
| JP | 2-86036 | 3/1990 |
| JP | 2-183150 | 7/1990 |
| JP | 7-151836 | 6/1995 |
| JP | 8-507640 | 8/1996 |
| JP | 9-500486 | 1/1997 |
| JP | 11-187900 | 7/1999 |
| WO | WO 94/20978 A1 | 9/1994 |

OTHER PUBLICATIONS

Mark Schena et al., "Quantitative Monitoring of Gene Expression Patterns with a Complementary DNA Microarray," 270 *Science* 467-470 (Oct. 1995).
H.F. Arlinghaus et al., "TOF-SIMS Characterization of DNA and PNA Biosensor Chips," *Proceedings of the 12th International Conference on Secondary Ion Mass Spectrometry*, pp. 951-954 (Sep. 1999).
Steven M. Hues et al., "A Pulsed Alkali-Ion Gun for Time-of-Flight Secondary Ion Mass Spectrometry," 60(7) *Rev. Sci. Instrum.* 1239-44 (Jul. 1989).
Viswanatham Katta et al., "A Pulsed Ion Bombardment Time-of-Flight Mass Spectrometer with High Sensitivity for the Analysis of Peptides," 105 *Int. J. Mass Spectrom. Ion Processes* 129-45 (1991).
J. Schwieters et al., "High Mass Resolution Surface Imaging with Time-of-Flight Secondary Ion Mass Spectroscopy Scanning Microprobe," 9(6) *J. Vac. Sci. Technol.* 2864-71 (1991).
Robert W. Odom, "Secondary Ion Mass Spectrometry Imaging," 29(1) *Appl. Spectros. Rev.* 67-116 (Feb. 1994).
J. Claereboudt et al., "Mass Spectral Behavior of (M-H)- Ions of Some Pyrimidine Nucleotides," 22 *Biol. Mass. Spectr.* 419-21 (1993).
H.F. Arlinghause et al., "Analysis of Biosensor Chips for Identification of Nucleic Acids,"69(18) *Anal. Chem.* 3747-53 (1997).
G.C. Rider et al., "Imaging Time-of-Flight SIMS—A New Technique for Spatially-Resolved Chemical Surface Analysis," 4(1) *J. Molecul. Electron.* 402 (1988) (Abstract).
Anthony J. Nicola et al., "Enhancement of Ion Intesnity in Time-of-Flight Secondary-Ionization Mass Spectrometry," 7 *J. Am. Soc. Mass Spectrom.* 467-71 (1996).

* cited by examiner

*Primary Examiner*—John S. Brusca
*Assistant Examiner*—Eric S. DeJong
(74) *Attorney, Agent, or Firm*—Fitzpatrick, Cella, Harper & Scinto (57) ABSTRACT

A measurement method is provided, which enables to obtain a two-dimensional image with better quantitative-ability by suppressing the influence of the charge-up, when the two-dimensional secondary ion image is obtained for a biological material fixed on a substrate having a high resistivity by utilizing a TOF-SIMS method in a certain wide area. A two-dimensional image having considerably high positioning resolution-ability can be obtained by the procedure in which the pulsed primary ion beam is irradiated at a spot, and the pulse-wise spot-applications of the primary ion beam and the simultaneous detection of the secondary ion generated from the irradiated primary ion beam proceed along with a discontinuous scanning pattern, and eventually the results of these secondary ion measurements are reconstructed into a two-dimensional image in line with the aforementioned discontinuous scanning pattern.

16 Claims, 3 Drawing Sheets

FIG. 1D
$C_5H_5N_2O_2$  (thymine-H)$^-$

METHOD FOR ACQUIRING INFORMATION OF A BIOCHIP USING TIME OF FLIGHT SECONDARY ION MASS SPECTROMETRY AND AN APPARATUS FOR ACQUIRING INFORMATION FOR THE APPLICATION THEREOF

BACKGROUND OF THE INVENTION

1. Field of the Invention

The present invention relates to an imaging of a matrix disposed on a surface of a biochip, which includes a substrate and a plurality of biological materials disposed on a surface of the substrate in a matrix form, and also relates to an analysis of the components of the matrix.

2. Description of the Related Art

A biochip, such as a DNA chip, protein chip and so on, which includes a substrate and various molecular probes disposed on a surface of the substrate in a matrix form, has been employed for the purposes of analyzing a genome or analyzing a generation of a gene. Further, it is expected that the result of the analysis employing biochips provides a critical index for diagnosis of cancers, genetic diseases, lifestyle-related diseases, infectious diseases and the like, prediction for prognostics, or a decision on treatment policy and so on.

Several methods for preparing biochips are known. Exemplary methods for preparing a DNA chip may include: a method of consecutively synthesizing DNA probes directly onto a substrate by using photolithography (U.S. Pat. No. 5,405,783 and so on); or a method for supplying synthesized DNA or synthesized cDNA (complementary DNA) onto a substrate and binding it thereto (U.S. Pat. No. 5,601,980, Japanese Patent Laid-Open No H11-187,900 (1999), an article in "SCIENCE", Vol. 270, pp. 467 (1995) and so on).

In general, the biochip is formed by using one of the two methods described above, and when the thus-formed biochip is used for the applications described above, it is critical to know quantities, i.e., densities, of biological materials used for forming probes that are included in matrices for the purpose of ensuring the credibility of the analysis, i.e., the quantification or the reproducibility of the analysis. Further, it is also critical to know what type of matrix dimension (i.e., shape, size or condition) is provided to the matrix existing thereon (i.e., imaging) for the purpose of assuring the quantification-ability or the reproducibility of the analysis. In addition, as described later, if there is no physical address for indicating the expected position of a matrix on the substrate that is employed for forming chips, an additional problem may occur. More specifically, when the biochip is formed by using a method of supplying fine droplets of a probe solution thereto via the ink jet method, for example, an absence of the physical address thereon may lead to an unclear determination of the position of the probe portion when the analysis is conducted on the biochip, depending on employed method. In such case, the detection means itself must also enable a clear determination of the matrix position.

However, the probe on the biochip exists principally as a monolayer or less, and in general, the analysis of the biological materials including the clear determination of the matrix position requires highly sensitive surface analysis techniques.

One of the known highly sensitive surface analysis techniques that satisfies the aforementioned requirements may be a method of using stable isotope labeled probes. However, this method has various disadvantages from the viewpoint of general purpose usage. Specifically the method requires complicated labeling, as well as special facilities and special equipment, because the employed isotope itself may be a source of a radioactive emission.

Another method may be that of labeling the probe with a fluorescent label, or alternatively, that of labeling a specific material that specifically binds to the probe with a fluorescent label and then binding it to the probe, which is known as a fluorescent-hybridization method for the DNA chip. However, such a method also has various problems with respect to achieving higher quantification-ability, such as a problem of the chemical stability of the fluorescent dye used for labeling, a problem of the fluorescent quenching, a problem of the nonspecific adsorption of the fluorescent dye onto the substrate surface, or additionally the problem of the quantification-ability (i.e., stability, reproducibility) of the specific binding-ability (i.e., hybridization) Thus, there are a number of problems for quantitatively detecting the amount of the existing probe itself.

Other highly sensitive surface analysis methods that are capable of being employed for analyzing general detection objects include the ATR method that utilizes FT-IR (Fourier Transform Infra Red Spectroscopy), XPS (X-ray Photoelectron Spectroscopy) and so on. However, these methods do not involve sufficient sensitivity for the quantitative analysis of the probe on a biochip, i.e., a biological material, or imaging thereof. In particular, when a general purpose glass is employed as a substrate for producing the biochip, these methods are not available, because the absorption due to the glass substrate itself adversely affects the analysis results when the FT-IR (ATR) method is employed, for example, or because a charge-up occurred on the glass, which is an electrically insulating material, adversely affecting the analysis when the XPS method is employed.

Yet another highly sensitive surface analysis method that is capable of being employed for analyzing biological related materials may be a DNA detection method utilizing the laser RIS (Resonance Ionization Spectroscopy) method, which is disclosed in U.S. Pat. No. 5,821,060. In this method, the specimen surface is irradiated with laser or ion beams mentioned below, and the generated portion is irradiated with a laser beam having a wavelength that is equivalent to ionization energy of a specific element, so that the specific element is ionized and emitted from the specimen surface and the emitted ionized element is detected. Disclosed methods for releasing the element from the specimen surface may be a method utilizing a laser beam (laser ablation) or a method utilizing ions (ion sputtering). However, these methods have a technical limitation in that only a limited number of elements can be detected.

Yet another highly sensitive surface analysis method may be dynamic SIMS (Secondary Ion Mass Spectrometry), in which an organic compound is decomposed to smaller fragment ions or to particles during the process of generating a secondary ion. Thus, the amount of the information on the chemical structures obtained from the mass spectrum is not sufficient. Thus, the method is not generally suitable, because the obtained information is not sufficient for the analysis of organic compounds such as, for example, nucleic acid-related materials having only four common bases.

On the other hand, the time of flight secondary ion mass spectrometry (TOF-SIMS), which is also known as another technique of the secondary ion mass spectrometry, is an analysis method for investigating what types of atoms or molecules exist on the uppermost surface of a solid specimen. This method has the following advantages: having an ability to detect a trace amount of a component of $10^9$ atoms/cm² (equivalent to 1/10⁵ of all atoms existing in one atomic layer of the uppermost surface); being applicable to both organic and inorganic compounds; being capable of detecting all types of elements and compounds that exist on the surface; and being able to image secondary ions from materials that are on the surface of the specimen.

Here, the principles of the time of flight secondary ion mass spectrometry will be described as follows.

At high vacuum, a high speed pulsed ion beam (primary ion) irradiated to a surface of a solid specimen causes sputtering, in which a structural component of the surface is emitted into the vacuum. Ions (secondary ions) having positive or negative charges generated during this process are accelerated into a mass spectrometer, where they are mass-analyzed by measuring the travel time from the specimen surface to a detector. In the sputtering process, various ions having a variety of masses are generated depending on the chemical components of the surface of the specimen, and the ions having a smaller mass fly faster and, on the contrary, ions having a larger mass fly slower, within a constant electrical field. Thus, detecting the time elapsed from the generation of the secondary ions to the arrival of the generated ions to the detector (i.e., time of flight) provides an analysis of the mass of the generated secondary ions.

On the other hand, in the dynamic-SIMS method, organic compounds are decomposed to small fragment ions or particles during the ionization process as stated above. Thus, information on the chemical structure obtained from the mass spectrum, e.g., mass range, is limited. On the contrary, in the TOF-SIMS method, the structures of the organic compounds can be directly obtainable from the mass spectrum with a wide mass range, because a much smaller amount of the primary ions is necessary in the TOF-SIMS method, so that while the organic compounds are ionized, they substantially retain their chemical structure. In addition, the information on the uppermost layer (within a depth of several angstroms) of the object can be selectively obtained as only the secondary ions generated in the uppermost solid surface are emitted into the vacuum.

The TOF-SIMS apparatus that employs the principle of the measurements described above is generally classified as a sector-type apparatus and a reflectron-type apparatus. One of the differences between these two types is in the manner of electrically grounding of a holder that fixes an object to be analyzed. In the sector-type apparatus, the generated ions are led to the mass spectrometer by applying positive or negative voltage of several kV to the specimen-fixing holder. In the reflectron-type apparatus, the specimen-fixing holder is grounded and the secondary ions are led to the mass spectrometer by applying positive or negative voltage of several kV to several-ten kV to an extracting electrode for the secondary ions.

The TOF-SIMS method often utilizes positive primary ions, and both positive secondary ions and negative secondary ions are generated regardless of the polarity of the utilized primary ions. Also, regardless of the polarity of the utilized primary ions, the amount of the secondary electrons that are generated by irradiating the primary ions is greater than the primary ions under the general measurement conditions, so that the surface potential tends to be positive. In turn, when the positive charge accumulates beyond a certain level (i.e., charge-up condition), the excessive positive charge may disturb the quantitative measurements. In considering the apparatus configurations in relation with the charge-up condition, the measurements of the negative secondary ions from the insulator material by using the sector-type apparatus can cause the highest positive-charge accumulation, because all of the generated secondary electrons are directed toward the extracting electrode for the (negative) secondary ions, wherein the above-mentioned positive voltage is applied to the extracting electrode.

In order to neutralize the positive charge caused by the above-mentioned charge-up condition, both the sector-type apparatus and the reflectron-type apparatus may often be equipped with a pulse-type electron gun for neutralizing the charge. A specific method for neutralizing the charge by using the pulse-type electron gun may include a step of applying the electron beam from the above-mentioned pulse-type electron gun onto the object to be analyzed for a constant duration irradiating primary ions (sub-nanosecond pulse to several nanosecond pulse) and before irradiating the primary ions for the next process of generating secondary ions. Here, while the electron beam is irradiated by the pulse-type electron gun onto the object to be analyzed, the application of the voltage to the object holder (for the sector-type apparatus) or to the secondary ion extracting electrode (for the reflectron-type apparatus) is stopped, and the holder or the electrode is grounded, respectively.

The above-mentioned method of neutralizing the charge often relieves (or compensates for) the accumulated positive charge, enabling the analysis of the insulator material. Here, when the negative secondary ions are measured for the insulator material by using the sector-type apparatus, the insulator is most-considerably and positively charged, and thus the margin of the charge-neutralization in this type of measurement is the narrowest. In order to prevent the charge-up, using the reflectron-type apparatus, in which the object holder is constantly electrically grounded, is (in general) more advantageous than using the sector-type apparatus. In particular, when the object to be analyzed has a lower electric conductivity (in other words, higher electric resistivity or a lower dielectric constant), e.g., glass and the like, a reflectron-type apparatus is more suitable for carrying out the quantitative measurements.

Regardless of whether a reflectron-type apparatus or a sector-type apparatus is employed, the TOF-SIMS method is the analysis method of a considerably higher sensitivity. This method enables the analysis of an object and is less influenced by a charge-up, e.g., oligonucleotide formed in a single molecular film level on a gold substrate having better electric conductivity. (Proceeding of the 12th International Conference on Secondary Ion Mass Spectrometry, 951 (1999)). Further, an evaluation conducted by the present inventors shows that, by conducting the process of preventing the charging-up, biological materials such as oligonucleotide bound to the substrate surface with a higher dielectric constant, such as a glass substrate, can be in-situ analyzed by irradiating the primary ions at a spot several μm in diameter when the analysis is conducted by an individual spot measurement.

However, the evaluation conducted by the present inventors also shows that when the two-dimensional secondary ion image was to be obtained by sequentially scanning the primary ion beam having a beam diameter of 5 μm in a constant direction, like the scanning line of a TV receiver (i.e., raster scanning), onto the substrate of a higher resistivity across a wide area, e.g., the area that is 500 μm×500 μm, a good image was not obtained because of considerable influence of the charge-up.

SUMMARY OF THE INVENTION

The present invention provides a solution for the aforementioned problems. The present invention provides a measurement method, which enables one to obtain a two-dimensional image with better quantitative-ability by suppressing the influence of the charge accumulation when the two-dimensional secondary ion image is obtained for a biological material fixed on a substrate having high resistivity by utilizing a TOF-SIMS method over a wide area.

The present inventors have actively investigated the above-mentioned problems, i.e., looked for a solution for suppressing the influence of the charge-up when two-dimensional imaging is conducted via the TOF-SIMS method for a relatively large area of the portion of a biochip that includes a biological material formed on a substrate having a relatively high resistivity. The present inventors have found that a two-dimensional image having a considerably high positioning resolution-ability can be obtained by the procedure in which the pulsed primary ion beam is irradiated at a spot, and the pulse-wise spot-applications of the primary ion beam and the simultaneous detection of the secondary ion generated from the irradiated primary ion beam proceeded along with a discontinuous scanning pattern, and eventually these secondary ion measurements results are reconstructed into a two-dimensional image in line with the aforementioned discontinuous scanning pattern. Further, the present inventors have also confirmed that, when the pulsed primary ion beam is irradiated along with the aforementioned discrete pattern, the charge-up of some insufficiently charge-neutralized spots has dissipated until the detection of the secondary ion for the adjacent spots is conducted. Therefore, the present invention has been achieved on this basis.

That is, according to the present invention, a method for acquiring information in relation to a biochip, which includes a substrate and a plurality of biological-related materials disposed on a surface of the substrate, from the surface of the biochip using time of flight secondary ion mass spectrometry, includes at least the steps of:

irradiating a pulsed primary ion beam on the surface of the biochip in a discontinuous pattern, the surface of the biochip having the biological-related material disposed thereon, and the primary ion beam having a spot size of an area that is a much smaller area than the one to be measured on the surface of the biochip;

conducting mass-analysis of secondary ions via time of flight, the secondary ion being generated by irradiating the pulsed primary ion beam; and reconstructing analyzed results obtained by conducting the mass-analysis to form two-dimensional distribution information on the basis of the pattern of the applying primary ion beam in a pulse manner.

Further, a method for analyzing components on a biochip surface according to the present invention may be a method for analyzing components of a biological material disposed on a biochip, which includes a substrate and a plurality of biological materials disposed on a surface of the substrate, from the surface of the biochip using time of flight secondary ion mass spectrometry, including at least the steps of:

irradiating a pulsed primary ion beam on the surface of the biochip in a discontinuous pattern, the surface of the biochip having the biological material disposed thereon, and the primary ion beam having a spot size area that is much smaller than an area to be measured on the surface of the biochip;

conducting mass-analysis of secondary ions via time of flight, the secondary ion being generated by irradiating the pulsed primary ion beam;

reconstructing analyzed results obtained by conducting the mass-analysis to form two-dimensional distribution information on the basis of the pattern of the irradiating pulsed primary ion beam; and conducting component-analysis of the biological material of a necessary portion contained in the obtained two-dimensional image on the basis of the mass spectrum information of the necessary portion.

In addition, the present invention also provides an apparatus adopted to be used for acquiring information from the above-mentioned biochip surface, that is, an apparatus for acquiring information from the biochip surface according to the present invention may be an apparatus for acquiring information in relation to a biochip including a substrate and a plurality of biological-related materials disposed on a surface of the substrate from the surface of the biochip using time of flight secondary ion mass spectrometry, including at least:

a device for irradiating a pulsed primary ion beam on the surface of the biochip in a discontinuous pattern, the surface of the biochip having the biological-related material disposed thereon, and the primary ion beam having a spot size of a much smaller area than an area to be measured on the surface of the biochip;

a device for conducting mass-analysis of secondary ions via time of flight, the secondary ion being generated by irradiating the pulsed primary ion beam; and a device for reconstructing analyzed results obtained by conducting the mass-analysis to form two-dimensional distribution information on the basis of the pattern of the irradiating pulsed primary ion beam.

Further objects, features and advantages of the present invention will become apparent from the following description of the preferred embodiments with reference to the attached drawings.

BRIEF DESCRIPTION OF THE DRAWINGS

FIGS. 1-A, 1-B, 1-C and 1-D are images of the results of imaging according to Example 2, showing the imaging results obtained by reconstructing the data on the basis of $PO_2^-$ ion (FIG. 1-A); $PO_3^-$ ion (FIG. 1-B); $PO_2^-$ ion+$PO_3^-$ ion (FIG. 1-C); and (thymine-H)$^-$ ion (FIG. 1-D);

DETAILED DESCRIPTION OF THE INVENTION

The present invention will be fully described in detail as follows.

The method according to the present invention is characterized in irradiating pulsed primary ions on the basis of the discontinuous scanning pattern for acquiring the images via TOF-SIMS, not based on the above-mentioned raster scanning, and also characterized in carrying out the imaging by reconstructing the respective mass analysis results obtained by respective discrete pulse-application on the basis of the pattern of the discontinuous pulse-application of the primary ion. The technique of scanning in the discontinuous scanning pattern enables imaging of a relatively large area of the surface of the biochip that includes biological materials formed on the substrate having a relatively high resistivity.

The discontinuous scanning pattern may be any pattern that enables avoiding the influence of the charge-up. A typical discontinuous pattern may be a random pattern or a specifically programmed pattern. In such a case, although overlapping of a unit (hereinafter called "pixel") being irradiated with primary ion beam (having same shape as the shape of primary ion beam) with the adjacent pixel may be permitted, the overlapping of the pixels is not preferable, because it may cause duplicated irradiation for an identical point in one scan, so that the obtained data does not reflect the actual value. Thus, if a random number is employed by the computer for generating a random scanning pattern, the employed random number may preferably be one that is capable of providing a uniform scan across the area being irradiated. Also, a programmed specific pattern described above may optionally be used, if necessary. The programmed specific pattern described above may preferably have discrete scan path tracks, each of which is sufficiently discrete or separated to avoid the charge-up problem. If the scan path tracks of the programmed specific pattern are sufficiently discrete, an effect equivalent to the one obtained by employing the random scanning can be expected by employing the programmed specific pattern. However, if the intervals between the discrete scan path tracks are short, or more specifically, for example, if the irradiation is carried out onto alternate pixels, or, in other words, if the irradiated pixels are relatively closely disposed, the influence of the charge-up cannot sufficiently be avoided. Thus, when the above-mentioned "programmed specific pattern" is employed, the scan path tracks of the pattern may preferably be designed to be sufficiently discrete.

When an image is formed by using a mass spectrum of the thus-obtained respective pixels, reconstructing the data in the order of the measurements of the respective pixels may not provide a suitable image that appropriately reflects the actual condition, because the scanning of the primary ion beam is carried out in the discontinuous pattern, i.e., random pattern, specifically programmed pattern and so on. In such a case, the present invention provides a suitable image that appropriately reflects the actual conditions, by storing the irradiation pattern of the primary ion beam and reconstructing the obtained data on the basis of the stored irradiation pattern.

The combination of the discontinuous application of the primary ion beam and the reconstruction of the obtained data according to the present invention is considerably advantageous in the measurement using a substrate having a high resistivity in which the measurement is considerably influenced by the charge-up. On the other hand, the combination according to the present invention may not be fully advantageous in reality in the measurement using the substrate having a lower resistivity in which suitable imaging can be carried out by using ordinary raster scanning, because the combination of the discontinuous scanning and the reconstruction of the data requires a longer period of time to carry out than the ordinary raster scanning. In order to fully provide the advantages of the invention, the scanning technique may be selected depending on the resistivity of the substrate to be used. For example, the range of the resistivity of the materials for the substrate, in which the discontinuous scanning is considerably advantageous, is a volumetric resistivity of not less than $10^{10}$ ohm·cm (300K).

The volumetric resistivity of the substrate being preferably used for the substrate of the biochip may not be less than $10^{10}$ ohm·cm (300K), and such a substrate is the most suitable for applying the imaging method according to the present invention.

The species of the primary ion for the use in the present invention may preferably be a gallium ion ($Ga^+$) or a cesium ion ($Ce^+$), and, optionally, an Au ion ($Au^+$) and the like, in view of ionization efficiency, mass analysis resolution and so on. Here, the Au ion is more preferably used, because it provides the mass analysis with a considerably higher sensitivity. In such a case, the available ion is not limited to the Au ion. An $Au_2$ ion and an $Au_3$ ion may be also used. The sensitivity of the measurement often increases by selecting the Au ion A greater increase is achieved by selecting the $Au_2$ ion ($Au_2^+$). A much greater increase is achieved by selecting the $Au_3$ ion ($Au_3^+$), thus presenting more preferable measurements.

When the imaging is carried out by using TOF-SIMS, the measurement conditions of mass analysis resolution, area for analysis and time for analysis are not uniquely determined, because the conditions are closely and mutually related to pulse frequency of the primary ion beam, energy of the primary ion beam, pulse width of the primary ion beam, and the data handling ability of the computer employed for the image processing. However, each of these conditions should be within a range for enabling the analysis.

In view of the availability of the analysis, the pulse frequency of the primary ion beam used in the present invention may preferably be in the range from 1 kHz to 50 kHz, the energy of the primary ion beam may preferably be in the range from 12 keV to 25 keV, and the pulse width of the primary ion beam may preferably be from 0.5 ns to 10 ns.

In order to improve the measurement accuracy, the measurement should be completed in a short period of time (an order of several-tens of seconds to several tens of minutes) while maintaining the high mass resolution. For this reason, the measurement may preferably be carried out without using a highly-focused primary ion beam to complete the measurement in a short period of time. More specifically, it is not necessary to highly focus the aperture diameter of the primary ion beam to a sub-micron level by a relatively complicated operation. It may preferably be focused at the level ranging from 1 μm to 10 μm by a relatively simple operation. This diameter range is preferable, considering that the size of the respective matrix (also called "dot" or "spot") on the biochip to be analyzed according to the present invention normally has a circular shape having a diameter from 10 μm to 100 μm, or a rectangular shape that ranges from 10 μm×10 μm to 100 μm×100 μm.

The area for scanning is not uniquely determined, because it is related to other factors as mentioned above However, preferably, this area has a circular shape having a diameter within a range from 50 μm to 500 μm, or a rectangular shape that ranges from 50 μm×50 μm to 500 μm×500 μm.

The number of the irradiating primary ion beams, i.e., the pixels, in one specific scanning process depends on the size of scanning area, the diameter of the primary ion beam, the level of the overlapping of the pixels, or the frequency of the primary ion beam or the scanning time for one scan. These conditions automatically determine the number of the pixels composing the secondary ion image. In this sense, the secondary ion image may be composed of pixels within a range from 56×56 pixels to 1024×1024 pixels.

The outer size of a generally used biochip may be, for example, 1 cm×1 cm, 1 inch×1 inch (25.4 cm×25.4 cm) or slide glass size (e.g., 26 mm×76 mm), and the matrix may be disposed within this size. The sizes of the scanning areas illustrated above are not sufficiently wide for scanning across such sized biochip to image the entire surface thereof.

In such a case, a process of positional scanning (in general, called "stage scanning", as a stage having a substrate thereon is scanned in this scanning process) of the substrate may be optionally employed in addition to the primary ion beam to scan a wider area of the surface, as required. In this case, a longer period of time for analysis is required if a wider area is scanned. However, since the matrix does not usually cover the entire surface of the biochip, the necessary area for the analysis may be selected depending on the requirement, and the scanning area may preferably be circular with a diameter of 1 mm or greater or a rectangular shape of a dimension of 1 mm×1 mm or larger, or more preferably, circular with a diameter within a range from 10 mm to 30 mm.

As described above, the main feature of the present invention is the imaging of the biochip via TOF-SIMS. From a different perspective, the imaging of the present invention is carried out on the basis of the mass data of the fragments, which can be detected, measured and analyzed by using TOF-SIMS. From yet another perspective, the mass spectrum data can be principally extracted from the portion (or the pixel) in which the mass data of the biochip for imaging is detected. The present invention includes the component analysis of the portions in which the imaging is carried out and the positions thereof are specified. The imaging of the specified portions of the actually prepared biochip via this method enables the determination of the positions and the shapes, and the component analysis of the positions.

The biological material disposed on the biochip, which is imaged or component-analyzed according to the present invention, is not particularly limited and may be any material as long as the material can be imaged or component-analyzed according to the TOF-SIMS method of the present invention. According to the evaluation of the present inventors, nucleic acids and proteins are preferable for the analysis. Examples of the nucleic acids may include DNA such as oligodeoxynucleotides, polydeoxynucleotides, cDNA (complementary DNA) and so on, RNA, such as mRNA (messenger RNA), tRNA (transfer RNA), rRNA (ribosomal RNA) and so on, and nucleic acid analogues being typically represented by peptide nucleic acid (PNA), the molecular bone of which comprises peptides. Examples of the proteins may include oligopeptides, polypeptides, enzymes, antibodies and so on.

The biological material on the substrate may be in any form. However, it is preferably covalently bonded to the substrate surface, in view of the form of the use of the biochip (for example, the form of the hybridization in the case of the DNA chip) and the stability of, for example, the level of ionization during the analysis using TOF-SIMS method. Various methods are known for forming the covalent bond between the biological material and the substrate surface, and a suitable method can be selected form the known methods. An example of the method of forming the covalent bond is disclosed in the Japanese Patent Laid-Open No. H11-187,900 (1999).

Also, methods for sequentially synthesizing the nucleic acids and proteins on the solid phase materials are known for one form of forming the covalent bond, and these methods can be employed for preparing the biochip that is the object of the method according to the present invention.

Further, the method of covalently bonding the biological material to the substrate may also include a method of covalently bonding a first functional group included in the biological material, e.g., a nucleic acid or a protein, with a second functional group bonded to the surface of the substrate by supplying the biological material onto the substrate, wherein the second functional group is capable of reacting with the first functional group to form the covalent bond therebetween. The method of supplying the biological material onto the substrate for employing in the present invention may include the ink-jet method typically including the known piezo-jet method and the thermal jet method. Japanese Patent Laid-Open No. H11-187,900 (1999) also discloses a method of supplying a DNA probe onto a substrate by the thermal jet method.

It is necessary to detect the fragment ions that are specific to the above-mentioned biological materials as secondary ions in order to carry out the imaging and the component analysis of the biochip via the TOF-SIMS method. The fragment ion may be any ion, as long as it is specific to the biological material and is capable of being detected by the TOF-SIMS method.

The non-limiting examples of the biological materials and specific fragment ions are described below.

When the biological material is a nucleic acid, it must have the backbone consisting of diester phosphates. Therefore, the fragment ions of the nucleic acid may include P−, PO−, PO2− and PO3−, which are the fragment ions of the above-mentioned backbone of diester phosphate, and these ions are capable of being detected via the TOF-SIMS method.

Further, when the nucleic acid is DNA, the material should include adenine, thymine, guanine and cytosine, and thymine is replaced with uracil in the case of RNA. Also, PNA, an exemplary nucleic acid analogue, should include adenine, thymine, guanine and cytosine. Thus, fragment ions of these bases, i.e., (adenine-H)—, (thymine-H)—, (guanine-H)—, (cytosine-H)— and (uracil-H)— can be employed for the secondary ions.

PNA also has a backbone that constitutes peptides. Thus, fragment ions of peptides, such as CNO— ion or CN— ion, can be employed for the detection via the TOF-SIMS method.

When the biological material to be detected is a protein, the fragment ions of the peptides can be employed, because the backbone of the protein contains peptides, as in the case of PNA. In addition, fragment ions derived by the residual group of each amino acid can also be employed. Here, the efficiency of the detection for proteins is generally lower than the efficiency for nucleic acids, because the mass spectrum intensity of one species derived by one amino acid of protein, which consists of more than 20 types of amino acids, is lower than the mass spectrum intensity of one species derived by one base of nucleic acids, such as DNA, RNA and PNA, which consists of four bases.

In the method for acquiring information, a TOF-SIMS apparatus for the use in performing two-dimensional imaging and component analysis may be any type of TOF-SIMS apparatus, as long as the apparatus is capable of performing detection, two-dimensional imaging and composition analysis. Here, the reflectron type apparatus, in which the holder for fixing the substrate is usually grounded, is preferably employed, due to the need to effectively reduce the influence of the charge-up that occurs on the substrate during the handling of the insulator material, as stated above.

EXAMPLES

The present invention will be described more specifically by illustrating examples.

Example 1 Preparation of a Nucleic Acid Probe Chip by Using a dT40 Probe

A nucleic acid probe was prepared by using quartz glass, similarly as in the method described in the Japanese Patent Laid-Open No. H11-187,900 (1999).

(1) Washing of the Substrate

A 25.4 mm×25.4 mm synthesized quartz substrate mm was placed on a rack and immersed in a solution containing a detergent for ultrasonic washing (GPIII, commercially available from BRANSON) diluted to 10% with pure water for one night. Then, the substrate was ultrasonic-washed in the detergent solution for 20 minutes and then washed with water to remove the detergent. After being rinsed with pure water, the substrate was further ultrasonic-washed within a container containing pure water for 20 minutes. Next, the substrate was immersed in an aqueous solution of 1N sodium hydroxide that was pre-heated to 80° C. for 10 minutes. Sequentially, the substrate was washed with water and further washed with pure water, and the washed substrate was transferred for further processing without conducting a drying process.

(2) Surface Treatment

An aqueous solution of 1% wt. of N-β-(aminoethyl)-g-aminopropyltrimethoxysilane, KBM603 (commercially available from SHIN-ETSU CHEMICAL IND. CO. LTD.), which is a silane coupling agent having amino acids bonded thereto, was stirred at room temperature for 2 hours to achieve a hydrolysis of the methoxy group contained in the molecule of the silane compound. The substrate that was washed as described in the above section (1) was then immersed into the aqueous solution of the silane coupling agent for 1 hour, and after that the substrate was washed with pure water, and both sides of the substrate were dried by blowing nitrogen gas thereon. Next, the substrate was baked in an oven that was heated to 120° C., for 1 hour, and thereby, amino acids were eventually introduced onto the surface of the substrate.

Next, 2.7 mg of N-(Maleimidocaproyloxy)succinimide (commercially available from DOJINDO LABORATORIES, hereinafter called "EMCS") was dissolved into a solution of 1:1 (by volumetric ratio) of dimethyl sulfoxide (DMSO)/ethanol to prepare a solution having a concentration of 0.3 mg/ml. The substrate, which had been treated via the silane-coupling treatment, was immersed in the EMCS solution at room temperature for 2 hours to react the amino group, which is introduced to the substrate surface via the silane coupling treatment, with the succinimide group of EMCS. The reaction introduced a maleimide group derived from EMCS present on the substrate surface. The substrate was then picked up from the EMCS solution, was washed with the aforementioned DMSO/ethanol solution, was washed with ethanol, and then was dried by blowing nitrogen gas thereon.

(3) Synthesis of Probe DNA

Single strand nucleic acid of SEQ ID NO:1 (40 mer of dT) was synthesized by a DNA synthesis company (BEX CO. LTD.). Sulfanilic group (SH) was introduced to the 5' end of the single strand DNA of the base SEQ ID NO:1 by using a thiol modifier (available from GLENN RESEARCH CENTER). After the DNA synthesis, the deprotecting and the recovering of DNA were carried out according to the ordinary methods, DNA was purified by using HPLC. The processing from the synthesis to the purification was conducted by the aforementioned DNA synthesis company.

SEQ ID NO:1

5'HS—$(CH_2)_6$—O—$PO_2$—O-TTTTTTTTT TTTTTTTTTT TTTTTTTTTT TTTTTTTTTT 3'

(4) DNA Discharge by Using a Thermal Jet Printer and Binding of DNA to the Substrate The single-stranded DNA described in the above section (3) was dissolved into a solution, which contained 7.5% wt. of glycerin, 7.5% wt. of urea, 7.5% wt. of thioglycol, and 1% wt. of acetylene alcohol (under the product name of "ACETYLENOL EH", commercially available from KAWAKEN FINE CHEMICAL CO., LTD.), to obtain an eventual concentration of 8 μm.

Meanwhile, a printer head ("BC-50", commercially available from CANON CO. LTD.) for a bubble jet printer ("BJF-850", commercially available from CANON CO. LTD.), which employs a bubble jet method that is one of the thermal jet methods, was altered so that the altered printer head was capable of discharging several hundred ml of the solution. The altered printer head was mounted to a discharge drawing device, which was also altered so as to be capable of discharging the solution onto the flat quartz substrate. Several hundred ml of the above-mentioned DNA solution was transferred into an altered tank of the printer head, and the EMCS-treated substrate was mounted to the discharge drawing device to carry out a spotting operation onto the EMCS-treated surface of the substrate. Here, the discharge rate during the spotting operation was 4 pl/droplet, the area of the spotting operation was 10 mm×10 mm, and the spotting was carried out at 200 dpi for that area, i.e., the discharge was performed at a pitch of 127 μm. Under these conditions, the diameter of the spotted dot was approximately 50 μm.

After completing the spotting operation, the substrate was left in a humidifier chamber for 30 minutes so that the maleimide group of the substrate surface would react with the sulfanilic group (SH) of the 5' end of the nucleic acid probe to fix the DNA probe thereon. Then, the substrate was washed with and stored in pure water. The obtained DNA-combined substrate (DNA chip) was dried by being blown on with nitrogen gas and was stored in a vacuum desiccator to be further dried just before conducting the analysis via TOF-SIMS.

Example 2 Imaging and Composition Analysis Via TOF-SIMS (1) Operations

The imaging and the composition analysis for the DNA chip prepared in the above-mentioned Example 1 were carried out by using a "TOF-SIMS IV" apparatus, which is commercially available from ION TOF CO. LTD.

The apparatus and conditions used in this operation are listed below.

<primary ion> primary ion beam: 25 kV, $Ga^+$, 0.6 pA (pulse current), random scan mode;

pulse frequency of the primary ion beam: 2.5 kHz (400 μsec./shot);

pulse width of the primary ion beam: 1 ns; and beam diameter of the primary ion beam: 5 μm.

<secondary ion: imaging was carried out by reconstructing the obtained data according to the application pattern of the primary ion beam> detection mode for secondary ion: negative;

area for the measurement: 300 μm×300 μm;

number of pixel in the secondary ion image: 128×128 pixels; and number of integrating operation: 256.

(2) Measurement Results

FIG. 1 shows the results of the imaging for the typical ion species from the data obtained by analyzing the DNA chip prepared in the Example 1 using the "TOF-SIMS IV"apparatus under the conditions described above. FIG. 1-A and FIG. 1-B represent the results of imaging of the $PO_2^-$ ion and the $PO_3^-$ ion, respectively, both of which are the fragment ions of DNA phosphate backbones. As can be seen from these two-dimensional images, it was confirmed that DNA was present on the DNA chip in spotted form deposited by using a bubble jet device (i.e., a substantially circular shape having a diameter of about 50 mm, and the pitch between the dots being about 125 μm). It is also possible to obtain a two-dimensional image by using the sum of the $PO_2^-$ ion and the $PO_3^-$ ion, as shown in FIG. 1-C, as well as the imaging of one fragment ion species.

It is also possible to conduct imaging by using a $C_5H_5N_2O_2^-$ ion, which is the fragment ion derived from the nucleic acid base, for example, as shown in FIG. 1-D, as well as one using the fragment ion of a phosphate backbone. Since the probe DNA used in the present example was a homo-oligomer of thymidylic acid, the detected fragment ion derived from the nucleic acid base was only the $C_5H_5N_2O_2^-$ ion, i.e., (thymine-H)$^-$ ion.

Figure 1A:
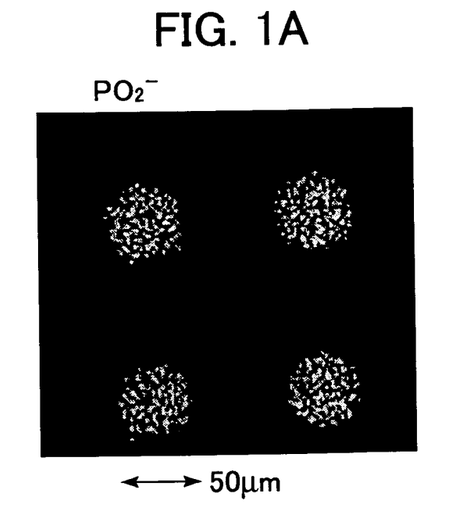
Figure 1B:
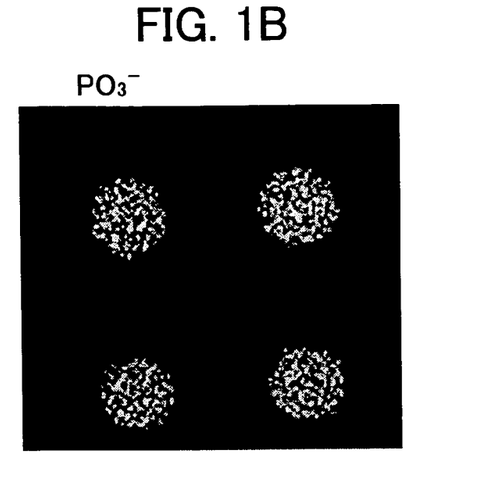
Figure 1C:
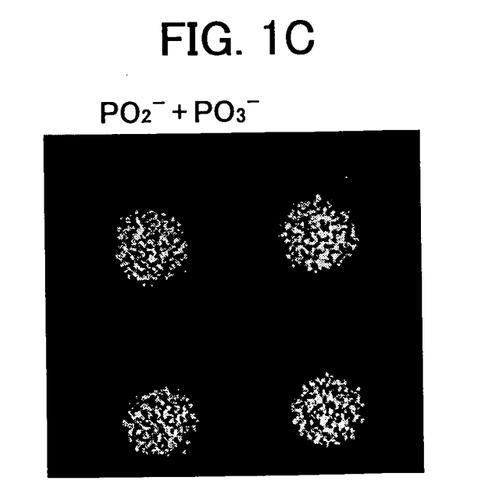
Figure 1D:
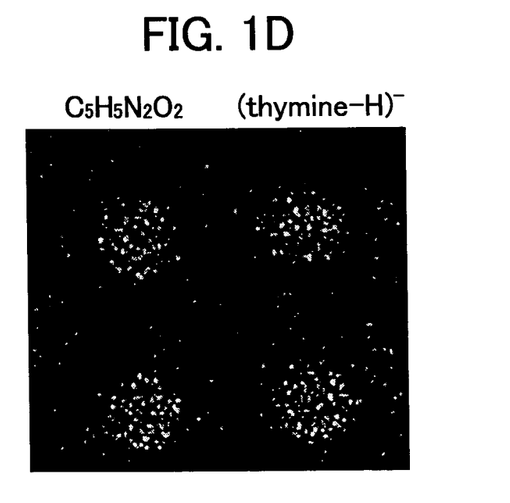
Figure 2:
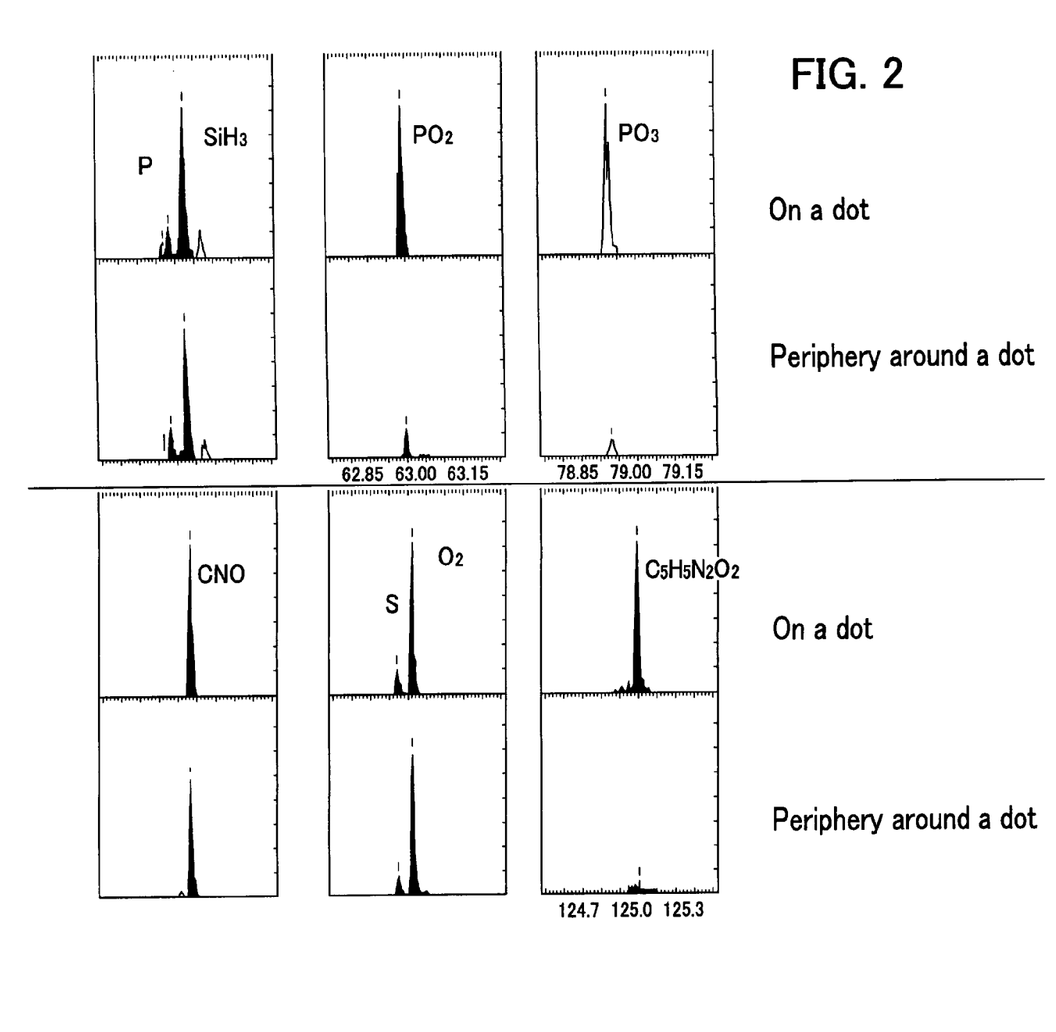
FIG. 2 is a graph showing the results of mass spectrum employed for obtaining the results of component analysis conducted in Example 2.

FIG. 2 shows mass spectrum profiles for the inner portion and the outer portion of a dot included in the obtained images concerning the typical secondary ions. For example, if the fragment ion is a $SiH_3$ ion, the presence of the ion is detected equally in either the inner portion or the outer portion of the dot, because the $SiH_3$ ion is not specific to the DNA existing inside the dot. To the contrary, if the fragment ion is $O2^-$, $P^-$, $PO^-$, $PO_2^-$, $PO_3^-$, $CNO^-$ (derived from the nucleic acid base) and $C_5H_5N_2O_2^-$, which are specific to the DNA existing inside the dot, or, in other words, if the probability of the ion existing inside the dot is higher than the probability of existing outside the dot, the intensity of the detected ion strength for these ions is stronger inside the dot than outside the dot. As seen in the results shown in FIG. 2, the use of the present invention enables the component analysis of the portion, the position of which is determined, by conducting the two-dimensional imaging via the mass spectroscopy.

Example 3 Preparation of a Nucleic Acid Probe Array by Employing 50 Mer Probe Containing Mixed Four Types of Nucleic Acid Bases, Imaging and Component Analysis Thereof (1) Preparation of DNA Chip DNA chip was prepared with DNA of the following SEQ ID NO:2, in the procedure identical to the procedure described in Example 1.

SEQ ID NO:2

5'HS—(CH$_2$)$_6$—O—PO$_2$—O-TGCAGGCATG CAAGCTTGGC ACTGGCCGTC GTTTTACAAC GTCGTGACTG 3'

(2) Imaging and Composition Analysis Via TOF-SIMS

Imaging and composition analysis for the DNA chip comprising DNA of the above-identified SEQ ID NO:2 were conducted via the method and conditions identical to these described in Example 2.

The results show that the imaging and the component analysis by the respective fragment ions of (adenine-H)$^-$, (guanine-H)$^-$ and (cytosine-H)$^-$ can be conducted, as well as the imaging and the component analysis for the fragment ions for the phosphate backbone and the fragment ions, such as (thymine-H)$^-$ described in Example 2.

Example 4 Preparation of RNA Chip, Imaging and Component Analysis Thereof (1) Preparation of RNA Chip RNA chip was prepared with RNA (U20) of the following SEQ ID NO:3 using a procedure that is identical to the one described in Example 1, except that all the preparation processes were carried out free of RNase that is an RNA decomposition enzyme.

SEQ ID NO:3

5'HS—(CH$_2$)$_6$—O—PO$_2$—O-UUUUUUUUUU UUUUUUUUUU 3'

(2) Imaging and Composition Analysis Via TOF-SIMS

Imaging and composition analysis for the RNA chip comprising RNA of the above-identified SEQ ID NO:3 were conducted via the method and conditions identical to those described in Example 2. Here, the RNA chip substrate was maintained RNase free just until the TOF-SIMS analysis was started.

The results of the present Example show that the imaging and the component analysis by the fragment ion of (uracil-H)– can be conducted, as well as the imaging and the component analysis for the phosphate backbone-derived the fragment ions in Example 2.

Example 5 Preparation of PNA Chip, Imaging and Component Analysis Thereof (1) Preparation of PNA Chip PNA having the base sequence identical to the base sequence of the DNA probe prepared in the Example 3 (referred to as SEQ ID NO:5) was synthesized by a DNA synthesis company (BEX CO. LTD.). Here, cysteine, one of the amino acids, was bonded to the N end (corresponding to the 5' end of nucleic acid) via a linker described below. Since cysteine contains a (SH—) group in the branch, PNA can bind with the maleimide group present on the quartz substrate after its surface is treated.

The PNA chip was prepared with PNA of SEQ ID NO:5 using a procedure identical to that in Example 1.

SEQ ID NO:5

NCys-NH—(CH$_2$)$_2$—O—(CH$_2$)$_2$—O—CH$_2$CONH-TG-CAGGCATG CAAGCTTGGC ACTGGCCGTC GTTTTA-CAAC GTCGTGACTG (2) Imaging and Composition Analysis Via TOF-SIMS Imaging and composition analysis for the PNA chip comprising PNA of the above-identified SEQ ID NO:5 were conducted via the method and conditions identical to those described in Example 2.

The results show that the imaging and the component analysis by the respective fragment ions of (adenine-H)$^-$, (thymine-H)$^-$, (guanine-H)$^-$ and (cytosine-H)$^-$, derived from four bases that constitute PNA, can be conducted. Here, since PNA has no phosphate backbone, no fragment ion derived from the phosphate backbone was detected. To the contrary, the fragment ions derived from the peptide bonds in the backbone of PNA, for example, CNO⁻ ions and CN⁻ ions, were detected.

Example 6 Preparation of Protein Chip, Imaging and Component Analysis Thereof (1) Preparation of Protein Chip A protein chip was prepared by fixing a protein on a quartz substrate surface using a method different from the methods for preparing synthesized nucleic acid probes described in Examples 1–5. More specifically, bovine serum albumin (BSA: commercially available from SIGMA ALDRICH JAPAN) was used. Here, BSA contains a cysteine residual group. Thus, the protein was bound to the substrate surface via the reaction of SH— of cysteine and the maleimide group on the substrate surface.

Spotting of a protein solution was carried out as in Example 1 to prepare the protein chip. Here, the conditions, such as the solvent and the BSA concentration during the discharging process of the BSA via the bubble jet, were accordingly adjusted.

(2) Imaging and Composition Analysis Via TOF-SIMS

Imaging and composition analysis for the protein chip comprising the above-identified BSA fixed thereto were conducted via the method and conditions identical to those described in Example 2, except that the detection mode for the secondary ion was selected to be positive.

The results show that the imaging and the component analysis by several fragment ions of residual groups of amino acids can be conducted. Typical secondary ion species were: $C_4H_8N^+$ and $C_4H_6N^+$, which are considered to be fragment ions derived by proline (Pro), $CH_3N^+$, $C_2H_7N_3^+$, $C_4H_{10}N_3^+$, $C_4H_{11}N_3^+$ and $C_5H_8N_3^+$, which are considered to be fragment ions derived by an arginine (Arg) residual group; and $C_9H_8N^+$, $C_{11}H_8NO^+$ and $C_4H_8NO^+$, which are considered to be fragment ions derived by a tryptophan (Trp) residual group. Further, $C_2H_6NS^+$ and $CHS^+$, which are considered to be fragment ions derived by a cysteine (Cys) residual group, were also detected. As can be seen from the results described above, the detection of the above-mentioned fragment ions, which are considered to be derived by amino acid residual groups, enables the imaging of the protein disposed on the insulator substrate surface. When the protein having characteristic amino residual groups is detected, an image equivalent to a two-dimensional distribution of the protein can be created by detecting the abovementioned fragment ions. Further, a combination of the image analysis and numerical analysis for an image created by the respective above-mentioned fragment ions, which are considered to be derived by respective amino acid residual groups (e.g., digitalization of the amount of the amino acids contained in the protein is conducted for a plurality of proteins is carried out and then the resultant digitalized data are correlated with the intensity of the above-mentioned fragment ions (i.e., image intensity)), can be carried out to obtain images (a two-dimensional distribution image) of respective proteins.

Example 7

Imaging and composition analysis for the DNA chip prepared in Example 1 were conducted via the method and conditions identical to that described in Example 2, except that the employed primary ion was Au⁺. The results show that the mass spectrum for the respective ions detected in Example 2 can be obtained with double-digit higher sensitivity and better imaging on the basis of the mass spectrum with higher sensitivity.

Example 8 Preparation of a Nucleic Acid Probe Array by Employing 13 Mer Probe Containing Mixed Four Types of Nucleic Acid Bases, Imaging and Component Analysis Thereof by Using TOF-SIMS Method with the Primary Ion Species of Ga⁺ and $Au_3^+$ (1) Preparation of DNA Chip A DNA chip was prepared with DNA of the following SEQ ID NO:4 using a procedure identical to that described in Example 1.

SEQ ID NO:4

5'HS—(CH₂)₆—O—PO₂—O-ACTGGCCGTC GTTTTACA 3'

(2) Imaging and Composition Analysis Via TOF-SIMS

Imaging and composition analysis for the DNA chip comprising DNA having the above-identified SEQ ID NO:4 were conducted by using Ga⁺ and $Au^{3+}$ for primary ions (apparatus employed for the present Examples was "TOF-SIMS IV" commercially available from ION TOF CO. LTD). The conditions for measurements are listed below.

Case of using Ga⁺ for primary ion species:

<primary ion> primary ion beam: 25 kV, Ga⁺, 0.6 pA (pulse current), random scan mode;

pulse frequency of the primary ion beam: 2.5 kHz (400 μsec./shot);

pulse width of the primary ion beam: approximately 1 ns; and beam diameter of the primary ion beam: 5 μm.

<secondary ion: imaging was carried out by reconstructing the obtained data according to the application pattern of the primary ion beam detection mode for secondary ion: negative;

area for the measurement: 300 μm×300 μm;

number of pixel in the secondary ion image: 128×128 pixels; and number of integrating operation: 256.

Case of using $Au_3^+$ for primary ion species:

<primary ion> primary ion beam: 25 kV, $Au_3^+$, 0.07 pA (pulse current), random scan mode;

pulse frequency of the primary ion beam: 5 kHz (200 μsec./shot);

pulse width of the primary ion beam: approximately 1 ns; and beam diameter of the primary ion beam: 5 μm.

<secondary ion: imaging was carried out by reconstructing the obtained data according to the application pattern of the primary ion beam> detection mode for secondary ion: negative;

area for the measurement: 300 μm×300 μm;

number of pixel in the secondary ion image: 128×128 pixels; and number of integrating operation: 281.

Figure 3:
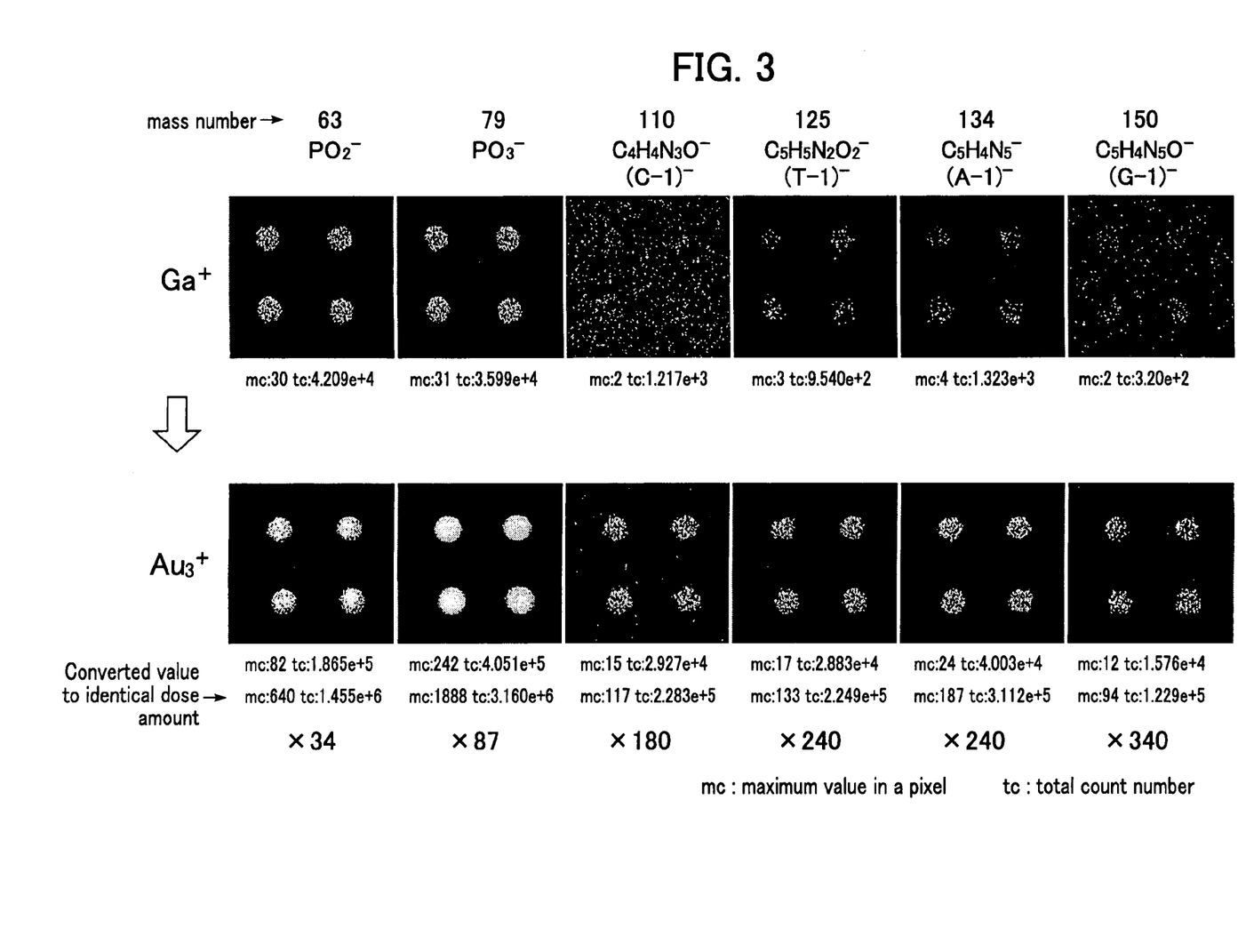
FIG. 3 shows images prepared from the results of Example 8, and the images shown in the upper row are obtained by using $Ga^+$, and the images in the lower row are obtained by using $Au_3^+$.

FIG. 3 shows the analysis results via TOF-SIMS obtained by using Ga$^+$ and Au$_3^+$ according to the conditions described above. FIG. 3 includes the images for PO$_2^-$, PO$_3^-$, C$_4$H$_4$N$_3^-$, C$_5$H$_5$N$_2$O$_2^-$, C$_5$H$_4$N$_5^-$ and C$_5$H$_4$N$_5$O$^-$, which are the typical secondary ions obtainable in the TOF-SIMS analysis for the DNA probe array containing four mixed types of nucleic acid bases by using Ga$^+$ (shown in upper row) or by using Au$_3$+(shown in a lower row). Here, the description "mc" refers the maximum value in a pixel, and "tc" refers to the total count number in the whole 128×128 pixels. As seen in these images, employing Au$_3^+$ provides a nearly double-digit higher sensitivity for PO$_3^-$ and also provides a greater than a double-digit sensitivity for the fragment ions derived from the four bases, compared to the case of employing Ga$^+$ (about 87-fold as reduced to the case of equivalent dosage, or about 20-fold as reduced to the case of equivalent measurement time (as 0.12-fold decrease in the pulse current, and 2-fold increase in the pulse cycle)). Thus, it was found that the use of the Au$_3^+$ gun for the TOF-SIMS analysis of the biochip was considerably advantageous.

While the present invention has been described with reference to what are presently considered to be the preferred embodiments, it is to be understood that the invention is not limited to the disclosed embodiments. To the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A method for acquiring information from a device, which comprises a substrate and a plurality of biological materials disposed on the surface of the substrate, wherein the information is acquired from the surface using time of flight secondary ion mass spectrometry, the method comprising at least the steps of:

irradiating the surface with a pulsed primary ion beam on different positions of the surface in a discontinuous pattern, which is a specifically programmed or a random pattern to suppress an influence of a charge-up of an irradiated area, wherein the irradiated area with the primary ion beam in one scan is not duplicated, and the primary ion beam has a beam size of a smaller area than an area to be measured on the surface of the device;

conducting mass-analysis of secondary ions via time of flight, the secondary ions being generated by irradiating the surface with the pulsed primary ion beam; and reconstructing analyzed results obtained by conducting the mass-analysis to form two-dimensional information on the basis of the pattern of the irradiating pulsed primary ion beam, wherein a volumetric resistivity of the substrate is not less than $10^{10}$ ohm·cm at 300K.

2. A method for acquiring information from a device, which comprises a substrate and a plurality of biological materials disposed on the surface of the substrate, wherein the information is acquired from the surface using time of flight secondary ion mass spectrometry, the method comprising at least the steps of:

irradiating the surface with a pulsed primary ion beam on different positions of the surface in a discontinuous pattern, which is a specifically programmed or a random pattern to suppress an influence of a charge-up of an irradiated area, wherein the irradiated area with the primary ion beam in one scan is not duplicated, the primary ion beam has a beam size of a smaller area than an area to be measured on the surface of the device, and a diameter of the primary ion beam is not larger than 10 µm;

conducting mass-analysis of secondary ions via time of flight, the secondary ions being generated by irradiating the surface with the pulsed primary ion beam; and reconstructing analyzed results obtained by conducting the mass-analysis to form two-dimensional information on the basis of the pattern of the irradiating pulsed primary ion beam.

3. An apparatus for acquiring information from a device, which comprises a substrate and a plurality of biological materials disposed on the surface of the substrate, wherein the information is acquired from the surface using time of flight secondary ion mass spectrometry, the apparatus comprising at least:

a means for irradiating the surface with a pulsed primary ion beam on the surface in a discontinuous pattern, which is a specifically programmed or a random pattern to suppress an influence of a charge-up of an irradiated area, wherein the irradiated area with the primary ion beam in one scan is not duplicated, and the primary ion beam having a beam size of a smaller area than an area to be measured on the surface of the device;

a means for conducting mass-analysis of secondary ions via time of flight, the secondary ions being generated by irradiating the surface with the pulsed primary ion beam; and a means for reconstructing analyzed results obtained by conducting the mass-analysis to form a two-dimensional information on the basis of the pattern of the irradiating pulsed primary ion beam, wherein a volumetric resistivity of the substrate is not less than $10^{10}$ ohm·cm at 300K.

4. An apparatus for acquiring information from a device, which comprises a substrate and a plurality of biological materials disposed on the surface of the substrate, wherein the information is acquired from the surface using time of flight secondary ion mass spectrometry, the apparatus comprising at least:

a means for irradiating the surface with a pulsed primary ion beam on the surface in a discontinuous pattern, which is a specifically programmed or a random pattern to suppress an influence of a charge-up of an irradiated area, wherein the irradiated area with the primary ion beam in one scan is not duplicated, the primary ion beam having a beam size of a smaller area than an area to be measured on the surface of the device, and a diameter of the primary ion beam is not larger than 10 µm;

a means for conducting mass-analysis of secondary ions via time of flight, the secondary ions being generated by irradiating the surface with the pulsed primary ion beam; and a means for reconstructing analyzed results obtained by conducting the mass-analysis to form a two-dimensional information on the basis of the pattern of the irradiating pulsed primary ion beam.

5. The method according to claim 1, wherein an ion species of the primary ion beam is a gold ion.

6. The method according to claim 1, wherein the device is a chip on which the biological materials are disposed.

7. The method according to claim 6, wherein one of the biological materials is a nucleic acid.

8. The method according to claim 6, wherein one of the biological materials is a protein.

9. The method according to claim 7, wherein the secondary ion species generated by the primary ion beam includes at least a species derived by fragmentation and ionization of a phosphate backbone derived from the nucleic acid.

10. The method according to claim 9, wherein the secondary ion species generated by the primary ion beam includes at least any one of $P^-$, $PO^-$, $PO_2^-$ and $PO_3^-$.

11. The method according to claim 2, wherein an ion species of the primary ion beam is a gold ion.

12. The method according to claim 2, wherein the device is a chip on which the biological materials are disposed.

13. The method according to claim 12, wherein one of the biological materials is a nucleic acid.

14. The method according to claim 12, wherein one of the biological materials is a protein.

15. The method according to claim 13, wherein the secondary ion species generated by the primary ion beam includes at least a species derived by fragmentation and ionization of a phosphate backbone derived from the nucleic acid.

16. The method according to claim 15, wherein the secondary ion species generated by the primary ion beam includes at least any one of $P^-$, $PO^-$, $PO_2^-$ and $PO_3^-$.

* * * * *

```
                        SEQUENCE LISTING

<160> NUMBER OF SEQ ID NOS: 5

<210> SEQ ID NO 1
<211> LENGTH: 40
<212> TYPE: DNA
<213> ORGANISM: Artificial sequence
<220> FEATURE:
<223> OTHER INFORMATION: Sample oligonucleotide

<400> SEQUENCE: 1
tttttttttt tttttttttt tttttttttt tttttttttt                        40

<210> SEQ ID NO 2
<211> LENGTH: 50
<212> TYPE: DNA
<213> ORGANISM: Artificial sequence
<220> FEATURE:
<223> OTHER INFORMATION: Sample oligonucleotide

<400> SEQUENCE: 2
tgcaggcatg caagcttggc actggccgtc gttttacaac gtcgtgactg             50

<210> SEQ ID NO 3
<211> LENGTH: 20
<212> TYPE: RNA
<213> ORGANISM: Artificial sequence
<220> FEATURE:
<223> OTHER INFORMATION: Sample oligonucleotide

<400> SEQUENCE: 3
uuuuuuuuuu uuuuuuuuuu                                              20

<210> SEQ ID NO 4
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 4
actggccgtc gttttaca                                                18

<210> SEQ ID NO 5
<211> LENGTH: 50
<212> TYPE: DNA
```

-continued

```
<213> ORGANISM: Artificial sequence
<220> FEATURE:
<221> NAME/KEY: misc_feature
<222> LOCATION: (1)..(1)
<223> OTHER INFORMATION: Sample oligonucleotide
<220> FEATURE:
<221> NAME/KEY: misc_feature
<222> LOCATION: (1)..(1)
<223> OTHER INFORMATION: n is NCys-NH-(CH2)2-O-(CH2)2-O-CH2CONH-T

<400> SEQUENCE: 5
ngcaggcatg caagcttggc actggccgtc gttttacaac gtcgtgactg            50
```